US010722441B2

(12) United States Patent
Carola et al.

(10) Patent No.: US 10,722,441 B2
(45) Date of Patent: Jul. 28, 2020

(54) NOREUGENIN GLYCOSIDE DERIVATIVES (71) Applicant: Universitaet Hamburg, Hamburg (DE)

(72) Inventors: Christophe Carola, Bensheim (DE);
Michael Schulte, Bischofsheim (DE);
Ulrich Rabausch, Hamburg (DE);
Henning Rosenfeld, Hamburg (DE);
Wolfgang Streit, Moenkeberg (DE)

(73) Assignee: Universitaet Hamburg, Hamburg (DE)

( * ) Notice: Subject to any disclaimer, the term of this patent is extended or adjusted under 35 U.S.C. 154(b) by 0 days.

(21) Appl. No.: 16/068,970

(22) PCT Filed: Dec. 16, 2016

(86) PCT No.: PCT/EP2016/002119
§ 371 (c)(1),
(2) Date: Jul. 10, 2018

(87) PCT Pub. No.: WO2017/121445
PCT Pub. Date: Jul. 20, 2017

(65) Prior Publication Data
US 2019/0029937 A1 Jan. 31, 2019

(30) Foreign Application Priority Data
Jan. 15, 2016 (EP) .................................. 16151433

(51) Int. Cl.
*A61K 8/60* (2006.01)
*A61Q 19/04* (2006.01)
*A61Q 17/04* (2006.01)
*A61Q 19/00* (2006.01)
*A61Q 19/08* (2006.01)

(52) U.S. Cl.
CPC .............. *A61K 8/602* (2013.01); *A61Q 17/04* (2013.01); *A61Q 19/00* (2013.01); *A61Q 19/04* (2013.01); *A61Q 19/08* (2013.01); *A61K 2800/78* (2013.01); *A61K 2800/85* (2013.01)

(58) Field of Classification Search
CPC ................................ A61K 8/602; A61Q 19/04
USPC ........................................................ 514/33
See application file for complete search history.

(56) References Cited

U.S. PATENT DOCUMENTS

| | | |
|---|---|---|
| 2005/0043398 A1 | 2/2005 | Carola et al. |
| 2009/0220438 A1 | 9/2009 | Carola et al. |
| 2010/0004209 A1 | 1/2010 | Carola et al. |
| 2013/0287716 A1 | 10/2013 | Carola et al. |

FOREIGN PATENT DOCUMENTS

| | | | |
|---|---|---|---|
| DE | 10337863 | A1 | 3/2005 |
| DE | 102006004327 | * | 8/2007 |
| EP | 2134732 | B1 | 11/2010 |
| WO | 2006094601 | A1 | 9/2006 |
| WO | 2007087956 | A1 | 8/2007 |
| WO | 2008025368 | A1 | 3/2008 |
| WO | 2012097857 | A1 | 7/2012 |
| WO | 2014191524 | A1 | 12/2014 |

OTHER PUBLICATIONS

Carola et al.; DE 102006004327 A1; Aug. 2, 2007 (Machine-English Translation).*
Written Opinion of the International Searching Authority dated Feb. 15, 2017, in International Application No. PCT/EP2016/002119.
International Search Report dated Feb. 15, 2017, in International Application No. PCT/EP2016/002119.
Kalia Rajwant K et al: "Understanding Tecomella undulata: an endangered pharmaceutically important timber species of hot arid regions", Genetic Resources and Crop Evolution, Kluwer, Dordrecht, NL, vol. 61, No. 7, Jun. 19, 2014 (Jun. 19, 2014), pp. 1397-1421, XP035402706, ISSN: 0925-9864, DOI: 10.1007/S10722-014-0140-3 [retrieved on Jun. 19, 2014] abstract, pp. 1400-140; table 1 p. 1406; table 2.
Database TKDL [Online] CSIR India; Jan. 1, 1928 (Jan. 1, 1928), NN: "Bh'tabhairavarasa a(1)", XP002766623, Database accession No. RD/707 Therapeutic composition; paragraph [0002], complexion promoting (var'ya); paragraph [0008].
Database TKDL [Online] CSIR India; Jan. 1, 1999 (Jan. 1, 1999), NN: "Nyagrodhcdyamgh"tam", XP002766624, Database accession No. RG/683 therapeutic composition; paragraph [0002], complexion promoting (var'ya); paragraph [0007].
Lubica Lacikova et al: "Antiproliferative, Cytotoxic, Antioxidant Activity and Polyphenols Contents in Leaves of Four *Staphylea* L. Species", Molecules Online, vol. 14, No. 9, Aug. 28, 2009 (Aug. 28, 2009), pp. 3259-3267, XP055338940, DE, ISSN: 1433-1373, DOI: 10.3390/molecules14093259, p. 3262; table 2, p. 3263, last paragraph, plant material and extraction; p. 3264.
Y.-B. Wang et al: "Chromone glycosides from Knoxia corymbosa", Journal of Asian Natural Products Research, vol. 8, No. 7, Oct. 1, 2006 (Oct. 1, 2006) , pp. 663-670, XP055338977, CH, ISSN: 1028-6020, DOI: 10.1080/10286020500246303 abstract, Introduction, figure 1; compounds 1-3.
Lifeng Han et al: "Triglyceride accumulation inhibitory effects of new chromone glycosides from Drynaria fortunei", Natural Product Research, vol. 29, No. 18, Sep. 17, 2015 (Sep. 17, 2015), pp. 1703-1710, XP055339792, GB; ISSN: 1478-6419, DOI: 10.1080/14786419.2014.998216 abstract, Introduction; p. 1703, Extraction and Isolation; p. 1707, paragraph 3.3. Acid hydrolysis of compounds 1 and 2; p. 1708, paragraph 3.4 figure 1; compounds 1,2,6,7.

(Continued)

*Primary Examiner* — Shaojia A Jiang
*Assistant Examiner* — Michael C Henry
(74) *Attorney, Agent, or Firm* — Patent Central LLC; Stephan A. Pendorf (57) ABSTRACT

A use of noreugenin glycoside derivatives of formulas I, II and III as a self-tanning substance or to increase the synthesis of melanin, improve melanin transport and/or improve the distribution of melanin in suprabasal layers, preparations containing noreugenin glycoside derivatives of formulas I, II and III, and noreugenin glycoside derivatives of formulas I, II and III.

9 Claims, 4 Drawing Sheets

(56) References Cited

OTHER PUBLICATIONS

Soon-J00 Sohn et al: "Chemical Constituents of the Leaves of Staphylea bumalda; Korea Science", Natural Product Sciences, vol. 10, No. 4, Jan. 1, 2004 (Jan. 1, 2004), pp. 173-176, XP055338850, Korea, compound 2, extraction and isolation; p. 173.

V.K. Gujral et al: "A new chromone glucoside from Tecomella undulata", Phytochemistry, vol. 18, No. 1, Jan. 1, 1979 (Jan. 1, 1979), pp. 181-182, XP055338836, GB; ISSN: 0031-9422, DOI: 10.1016/S0031-9422(00)90945-2; key word index; p. 181, last row; p. 182.

Suresh Kumar et al: "In vivo anti-hyperglycemic and antioxidant potentials of ethanolic extract from Tecomella undulata", Diabetology & Metabolic Syndrome, Biomed Central Ltd, London, UK, vol. 4, No. 1, Jul. 6, 2012 (Jul. 6, 2012), p. 33, XP021108263, ISSN: 1758-5996, DOI: 10.1186/1758-5996-4-33 abstract; figure 5.

Junichi Kitajima et al: "Pharmaceutical Society of Japan NII-Electronic Library Service Moneterpenoid Glucosidesof *Cnidium monnieri* Fruit", Chem. Pharm. Bull, Jan. 1, 1999 (Jan. 1, 1999), pp. 639-642, XP055338865, Retrieved from the Internet: URL:http://ci.nii.ac.jp/lognavi?name=nels&ang=en&type=pdf&id=ART0004118135, [retrieved on Jan. 25, 2017], figure 1; compound 8.

Database Medline [Online] US National Library of Medicine (NLM), Bethesda, MD, US; Sep. 2007 (Sep. 2007), Xue Jun-Yi et al: "[Studies on the chemical constituents of Adina pilulifera]", XP002766625, Database accession No. NLM18236749, abstract.

Zhong Yao Cai = Zhongyaocai = Journal of Chinese Medicinal Materials Sep 2007, vol. 30, No. 9, Sep. 2007 (Sep. 2007), pp. 1084-1086, ISSN: 1001-4454.

\* cited by examiner

NOREUGENIN GLYCOSIDE DERIVATIVES

The present invention relates to the use of noreugenin glycoside derivatives of formulas I, II and III as a self-tanning substance or to increase melanin synthesis, improve melanin transport and/or improve the distribution of melanin in suprabasal layers, preparations containing noreugenin glycoside derivatives of formulas I, II and III as well as noreugenin glycoside derivatives of formulas I, II and III themselves.

The trend away from a preference for pale skin to an "athletic, healthy-looking tan skin" has been uninterrupted for many years. To achieve a tanned tint, people expose their skin to sunlight because it causes pigmentation by formation of melanin. However, the UV radiation of sunlight also has a damaging effect on skin. In addition to acute damage (sunburn), there is also long-term damage from excessive exposure to light of the UVB range (wavelength 280-320 nm), such as an increased risk of developing skin cancer. Excessive exposure to UVB and UVA radiation (wavelength 320-400 nm) generates highly-reactive radical species that continue to multiply even after the sunlight exposure has stopped and result in wrinkles and aging of skin as a result.

Tanning (pigmentation) of skin offers natural protection against the negative consequences of sunlight exposure. The epidermis contains in its lowest layer, the basal layer, not only the basal cells but also individual pigment-forming cells known as melanocytes. In these cells, UV light stimulates production of melanin, which is transported into the keratinocytes (horny cells), where it becomes visible as a tan skin color. Melanin protects the cell nuclei from further exposure and prevents the negative effects thereby induced in cellular DNA.

Depending on the chemical composition of the pigments formed biochemically, a distinction is made between the brownish black eumelanin and the reddish yellow pheomelanin. The observed skin color is determined by the ratio of these two types of melanin. This pigment formed starting from the amino acid tyrosine is initiated primarily by UVB radiation and is known as "indirect pigmentation." It develops over a period of several days so the resulting tan lasts for a few weeks. In "direct pigmentation," which is used with sun exposure, mainly colorless melanin precursors are oxidized by UVA radiation to form dark-colored melanin. Since this oxidation is reversible, it leads to a tanning of the skin that lasts only a short period of time.

Artificial tanning of skin can also be produced externally with the help of makeup and orally by taking carotinoids.

However, the artificial tanning of skin that can be achieved by applying so-called self-tanning products is far more popular. These compounds contain keto- and/or acetaldehyde groups in proximity to alcohol functions as a chemical structural feature and most of them belong to the sugar class of substances. Self-tanning substances that are used especially often include 1,3-dihydroxyacetone (DHA) which is used in an amount of 700 metric tons annually, and erythrulose.

Self-tanning products can be reacted with the proteins and amino acids of the stratum corneum of the skin in the sense of a Maillard reaction or by means of a Michael addition reaction, wherein polymer products that impart a brownish tone to the skin are formed by means of a reaction pathway that still has not been completely elucidated. This reaction is concluded after about 4 to 6 hours. The tan thereby achieved cannot be washed off and is removed only with the normal desquamation of skin.

However, these tanning products do not themselves have any UV absorbing properties, so that additional protection from the sun (clothing, hat, UV filter) is necessary for sun exposure. In contrast with so-called "sun-tanned" skin, skin tanned with these products is not protected from sunburn.

Therefore, there continues to be a demand for dermatologically acceptable tanning substances, which are suitable for use in cosmetic and/or dermatologic preparations or medical products and which enhance the natural tanning of skin by increasing melanin synthesis, while at the same time permitting better skin protection and/or sun protection, in particular against UVB radiation.

So far, only a few such substances are known. WO 2012/097857 A1, for example, describes the use of 7-acyloxy chromen-4-one derivatives as self-tanning substances, which stimulate a natural tanning of skin.

The object on which the present invention is based was therefore to provide additional self-tanning substances that will stimulate the biological tanning of skin.

It has surprising been found that noreugenin glycoside derivatives are suitable as self-tanning substances.

In the sense of the present invention, the term self-tanning active ingredient is synonymous with self-tanning substance or self-tanner substance.

7-O-β-D-glucosylnoreugenin (7-(β-D-glucopyranosyloxy)-5-hydroxy-2-methyl4H-1-benzopyran-4-one or undulatoside A) (Ia) occurs naturally in various plants such as *Staphylea bumalda* (J. S. Soon et al., *Natural Product Science* (2004), 10(4), 173-176), *Tecomella undulata* (V. K. Gujral et al., *Indian Journal of Chemistry Section B-Organic Chemistry Including Medicinal Chemistry* (1979), 17, 40-41; S. Kumar et al. (2012), *Diabetology* & i Metabolic Syndrome, 4, 33), *Adina pilulifera* (H. W.-h. GUO Yue-wei et al. (2003), *Chinese Journal of Magnetic Resonance*, 20, 265-269) or in the fruits of *Cnidium monnieri* (J. Kitajina et al., *Chemical & Pharmaceutical Bulletin* (1999), 47(5), 639-642). There is no known cosmetic application of this substance.

Therefore, a first subject matter of the present invention is the use of at least one compound of formulas I, II or III wherein the R radicals, independently of one another, stand for a radical selected from the group comprising glucosyl, rhamnosyl, arabinosyl, galactosyl, galacturonide, glucuronide, 2-(acetylamino)-2-deoxyglucosyl, mannosyl, allosyl, fucosyl and xylosyl, wherein each of the radicals may be present as a D- or L-enantiomer and as α- or β-anomer, as a self-tanning substance.

The salts of the respective compounds according to formulas I, II or III are fundamentally also included by the designation "compound according to formulas I, II or III" in the sense of the present invention. The preferred salts include in particular alkali metal salts and alkaline earth metal salts, zinc salts as well as ammonium salts, but in particular sodium and potassium salts.

Compounds of formulas I, II or III may be used in self-tanning products as a self-tanning substance and/or to increase melanin synthesis in the skin, to improve the transport of melanin and/or to improve the distribution of melanin in suprabasal layers and/or to protect the skin from damaging UV radiation.

The subject matter of the present invention also includes the use of a compound of formulas I, II or III as described above to increase melanin synthesis, to improve melanin transport and/or to improve the distribution of melanin in suprabasal strata.

Compounds of formulas I, II or III increase the synthesis of melanin and improve the transport of melanin from the melanocytes to the keratinocytes. This affects the color of the skin and produces a tanning effect.

In the compounds of formulas I, II or III, the sugar radicals are each bound to the noreugenin radical by the OH group on the anomeric carbon.

The R radicals are preferably selected independently of one another from the group comprising glucosyl and rhamnosyl, wherein the radicals may each be present as the D- or L-enantiomer or as an α- or β-anomer.

A compound of formula I or II is preferably used.

The compound of formula I or II is also preferably selected from the compounds 7-O-β-D-glucosylnoreugenin (7-(β-D-glucopyranosyloxy)-5-hydroxy-2-methyl-4H-1-benzopyran-4-one) (Ia), 7-O-α-L-rhamnosylnoreugenin (7-[(6-deoxy-α-L-mannopyranosyl)oxy]-5-hydroxy-2-methyl-4H-1-benzopyran-4-one) (Ib) or 5-O-α-L-rhamnosylnoreugenin (5-[(6-deoxy-α-L-mannopyranosyl)oxy]-7-hydroxy-2-methyl-4H-1-benzopyran-4-one)(IIa):

(Ia)

(Ib)

(IIa)

The compounds of formula (Ia) (7-O-β-D-glucosylnoreugenin, 7-(β-D-glucopyranosyloxy)-5-hydroxy-2-methyl-4H-1-benzopyran-4-one or undulatoside A) occur naturally in various plants, for example, in *Staphylea bumalda* (J. S. Soon et al., *Natural Product Science* (2004), 10(4), 173-176) or in the fruit of *Cnidium monnieri* (J. Kitajina et al., *Chemical & Pharmaceutical Bulletin* (1999), 47(5), 639-642).

The compounds of formulas I, II or III can be synthesized by enzymatic glycosylation of noreugenin. Suitable enzymes are, for example, described in WO 2014/191524 A1:

These enzymes are the glycosyl transferases MgtB and GtfC from WO 2014/191524 A1. MgtB is used for the transfer of glucose radicals, the enzyme GtfC which can be expressed in recombinant form in *Escherichia coli*, is used for rhamnose transfer. Then the enzymatic reaction may take place as a whole-cell catalytic process or with isolated enzymes and pure substances. Whole-cell catalysis has the advantage that the necessary activated sugars, UDP glucose or TDP rhamnose are reconstructed permanently by the metabolism of the microorganisms. It would not present any problems to those skilled in the art to select suitable reaction conditions.

The compounds of formulas I, II or III may also have an antioxidant effect in addition to the skin tanning effect and are tolerated well by the skin. In addition, the compounds described here are preferably colorless or have only a faint color and therefore do not result in discoloration of the preparations. The preferred compounds also have an improved solubility in the aqueous phase of a preparation.

In order for the compounds of formulas I, II or III to be able to manifest their positive effect on the skin in a particularly favorable manner, it may be preferable to allow the compounds of formulas I, II or III as described above to penetrate into deeper strata of skin. Several possibilities are available for this. First, the compounds of formulas I, II or III may have a sufficient lipophilicity to be able to penetrate through the outer layer of skin into epidermal strata. As another possibility appropriate transport agents, such as liposomes, which enable transport of compounds of formulas I, II or III through the outer layers of skin may be present in the preparation. Finally, a systemic transport of compounds of formulas I, II or III is also conceivable. In that case, the preparation is designed to be suitable for oral administration.

The inventive use is preferably nontherapeutic.

Another subject matter of the present invention is a preparation containing at least one compound of formula I, II or III or the preferred embodiments thereof as described previously as well as a cosmetically suitable vehicle.

The preparations here are usually preparations that are applied topically, for example, cosmetic or dermatologic formulations or medical products. In this case the preparations contain a cosmetically or dermatologically suitable vehicle and may optionally contain additional suitable ingredients depending on the desired properties profile. If these products are pharmaceutical preparations, for example, then in this case the preparations will contain a pharmaceutically tolerable vehicle and optionally additional active pharmaceutical ingredients.

In the sense of the present invention, the term "agent" or "formulation" is also used as equivalent to the term "preparation."

The phrase "suitable for topical application" in the sense of the present invention means that the preparation is applied externally and locally, i.e., the preparation must be suitable for being applied to the skin.

The preparations may comprise or contain the aforementioned necessary or optional ingredients, may essentially consist thereof or may consist thereof. All the compounds or components that may be used in the preparations are either known and can be acquired commercially or they can be synthesized by known methods.

This is preferably a cosmetic or pharmaceutical preparation, especially preferably a cosmetic preparation.

The at least one compound of formula I, II or III is typically used in the preparations according to the invention in amounts between 0.01 to 10 wt %, preferably in amounts from 0.05 to 10 wt %, especially preferably in amounts from 0.1 wt % to 5 wt % and most especially preferably in amounts of 0.5 to 2 wt %, based on the total amount of the preparation. In addition, it would not present any problems for those skilled in the art to select the amounts as a function of the intended effect of the preparation accordingly.

Furthermore, the preparations according to the invention may also contain at least one additional self-tanning substance as an additional ingredient. This may be a self-tanning agent per se which reacts with the amino acids in skin in the sense of a Maillard reaction or reacts by way of a Michael addition to promote a so-called melanogenesis promoter or propigmentation active ingredient which promotes natural tanning of skin.

The following may be used, among others, as advantageous self-tanning substances: 1,3-dihydroxyacetone, glycerolaldehyde, hydroxymethylglyoxal, γ-dialdehyde, erythrulose, 6-aldo-D-fructose, ninhydrin, 5-hydroxy-1,4-naphthoquinone (Juglon) or 2-hydroxy-1,4-naphthoquinone (Lawson). Most especially preferred is 1,3-dihydroxyacetone, erythrulose or a synthetic combination thereof.

Propigmentation substances may in principle be any of the active ingredients with which those skilled in the art are familiar Examples include glycyrrhetinoic acid, melanocyte-stimulating hormone (α-MSH), peptide analogs, thymidine dinucleotides, L-tyrosine and ester thereof, bicyclic monoterpene diols (described by Brown et al., Photochemistry and Photobiology B: Biology, 63 (2001), 148-161) or 7-acyloxy chromen-4-one derivatives (described in WO 2012/097857 A1), in particular hexadecanoic acid 5-hydroxy-2-methyl-4-oxo-4H-chromen-7-yl ester (distributed by Merck KGaA, Darmstadt, Germany under the name Ronacare® Bronzyl™).

The at least one additional self-tanning substance is preferably present in the preparation in an amount of 0.01 to 20 wt %, especially preferably in an amount of 0.5 to 15 wt % and most especially preferably in an amount of 1 to 8 wt %, based on the total amount of the preparation.

Preparations having self-tanning properties, in particular those containing dihydroxyacetone, tend to develop an unpleasant odor when applied to human skin, presumably due to degradation products of dihydroxyacetone itself or caused by products of side reactions and are perceived as unpleasant by some users. It has been found that these unpleasant odors can be prevented by using formaldehyde scavengers and/or flavonoids. Therefore, the preparation according to the invention may also contain formaldehyde scavengers and optionally flavonoids to improve the odor.

The preparation according to the invention, which combines a self-tanning substance and a compound of formula I, II or III has the following advantage in comparison with a self-tanning product without the addition of a compound of formulas I, II or III:

Accelerated tanning reaction,
Lengthened tanning reaction because of the indirect tanning effect (UV-free tanning thereof),
Intensification of the tanning reaction,
Preventing uneven tanning due to careless application,
The tanning effect achieved approximates that of a natural tan,
Improving the protection against UV radiation.

The preparations according to the invention may also contain at least one UV filter in addition to the compounds of formula I, II or III.

Organic UV filters, so-called hydrophilic or lipophilic sun protection filters are effective in the UVA range and/or in the UVB range and/or in the IR and/or VIS range (absorbers). These substances can be selected in particular from cinnamic acid derivatives, salicylic acid derivatives, camphor derivatives, triazine derivatives, β,β-diphenyl acrylate derivatives, p-aminobenzoic acid derivatives as well as polymer filters and silicone filters as described in the patent application WO-93/04665. Additional examples of organic filters are given in European Patent Application EP-A 0 487 404. Most of the UV filters mentioned below are cited using INCI nomenclature.

Substances suitable for a combination in particular include: para-aminobenzoic acid and derivatives thereof: PABA, ethyl PABA, ethyl dihydroxypropyl PABA, ethylhexyl dimethyl PABA, e.g., distributed under the name "Escalol 507" by the company ISP, glyceryl PABA, PEG-25 PABA, e.g., distributed under the name "Uvinul P25" by BASF.

Salicylates: homosalates distributed under the name "Eusolex HMS" by Merck; ethylhexyl salicylates, e.g., distributed under the name "Neo Heliopan OS" by Symrise, dipropylene glycol salicylates, e.g., distributed under the name "Dipsal" by Scher, TEA salicylates, e.g., distributed under the name "Neo Heliopan TS" by Symrise.

β,β-Diphenyl acrylate derivatives: octocrylenes, e.g., distributed under the name "Eusolex® OCR" by Merck, "Uvinul N539" distributed by BASF, etocrylene, e.g., distributed under the name "Uvinul N35" by BASF.

Benzophenone derivatives: benzophenone-1, e.g., distributed under the name "Uvinul 400"; benzophenone-2, e.g., distributed under the name "Uvinul D50"; benzophenone-3 or oxybenzone, e.g., distributed under the name "Uvinul M40"; benzophenone-4, e.g., distributed under the name "Uvinul MS40"; benzophenone-9, e.g., distributed under the name "Uvinul DS-49" by BASF, benzophenone-5, benzophenone-6, e.g., distributed under the name "Helisorb 11" by Norquay, benzophenone-8, e.g., distributed under the name "Spectra-Sorb UV-24" by American Cyanamid, benzophenone-12, n-hexyl-2-(4-diethylamino-2-hydroxybenzoyl) benzoate or 2-hydroxy-4-methoxybenzophenone distributed by Merck, Darmstadt under the name Eusolex® 4360.

Benzylidene camphor derivatives: 3-benzylidene camphor, e.g., distributed under the name "Mexoryl SD" by Chimex, 4-methyl benzylidene camphor, e.g., distributed under the name "Eusolex 6300" by Merck, benzylidene camphor sulfonic acid, e.g., distributed under the name "Mexoryl SL" by Chimex, camphor benzalkonium methosulfate, e.g., distributed under the name "Mexoryl SO" by Chimex, terephthalylidene dicamphor sulfonic acid, e.g., distributed under the name "Mexoryl SX" by Chimex, polyacrylamidomethyl benzylidene camphor under the name "Mexoryl SW" by Chimex.

Phenylbenzimidazole derivatives: phenylbenzimidazole sulfonic acid, e.g., distributed under the name "Eusolex 232" by Merck, disodium phenyl dibenzimidazole tetrasulfonate, e.g., distributed under the name "Neo Heliopan AP" by Symrise.

Phenylbenzotriazole derivatives: drometrizole trisiloxane, e.g., distributed under the name "Silatrizole" by Rhodia Chimie, methylene-bis(benzotriazolyl) tetramethylbutyl phenol in solid form, e.g., distributed under the name "MIXXIM BB/100" by Fairmount Chemical, or in micronized form as an aqueous dispersion, e.g., distributed under the name "Tinosorb M" by BASF.

Triazinederivatives: ethylhexyltriazone, e.g., distributed under the name "Uvinul T150" by BASF, diethylhexylbutamidotriazone, e.g., distributed under the name "Uvasorb HEB" by Sigma 3V, 2,4,6-tris(diisobutyl-4'-aminobenzalmalonate) s-triazine or 2,4,6-tris-(biphenyl)-1,3,5-triazine distributed as "Tinosorb A2B" by BASF, 2,2'-[6-(4-methoxyphenyl)-1,3,5-triazine-2,4-diyl]-bis[5-(2-ethylhexyl)oxy] phenol, distributed as "Tinosorb S" by BASF, N2,N4-bis[4-[5-(1,1-dimethyl-propyl)-2-benzoxazolyl]phenyl]-N6-(2-ethylhexyl)-1,3,5-triazine-2,4,6-triamine distributed as "Uvasorb K 2A" by Sigma 3V or tris-biphenyltriazine distributed under the name "Tinosorb® A2B" by BASF.

Anthraniline derivatives: menthyl anthranilate, e.g., distributed under the name "Neo Heliopan MA" by Symrise.

Imidazole derivatives: ethylhexyl dimethoxybenzylidene dioxoimidazoline propionate.

Benzmalonate derivatives: polyorganosiloxanes containing functional benzmalonate groups such as polysilicone-15, e.g., distributed under the name "Parsol SLX" by Hoffmann LaRoche.

4,4-Diarylbutadienederivatives: 1,1-dicarboxy-(2,2'-dimethylpropyl)-4,4-diphenylbutadiene.

Benzoxazole derivatives: 2,4-bis[5-(1-dimethylpropyl)benzoxazol-2-yl-(4-phenyl)imino]-6-(2-ethylhexyl)imino-1,3,5-triazine, e.g., distributed under the name Uvasorb K2A by Sigma 3V and mixtures thereof.

Piperazine derivatives such as, for example, the compound or the UV filters of the following structures UV filters based on polysiloxane copolymers with a random distribution according to the following formula may also be used, wherein, for example, a=1.2; b=58 and c=2.8:

The compounds included in the list are to be regarded only as examples. Other UV filters may of course also be used.

Suitable organic UV-protective substances are preferably selected from the following list: ethylhexyl salicylate, phenylbenzimidazole sulfonic acid, benzophenone-3, benzophenone-4, benzophenone-5, n-hexyl 2-(4-diethylamino-2-hydroxybenzoyl) benzoate, 4-methylbenzylidene camphor, terephthalylidene dicamphorsulfonic acid, disodium phenyldibenzimidazole tetrasulfonate, methylene-bis(benzotriazolyl)tetramethylbutylphenol, ethylhexyl triazone, diethylhexyl butamidotriazone, drometrizole trisiloxane, polysilicone-15, 1,1-dicarboxy(2,2'-dimethylpropyl)-4,4-diphenylbutadiene, 2,4-bis[5-1-(dimethylpropyl)benzoxazol-2-yl-(4-phenyl)imino]-6-(2-ethylhexyl)imino-1,3,5-triazine and mixtures thereof.

These organic UV filters are generally incorporated into formulations in an amount of 0.01 wt % to 20 wt %, preferably 1 wt % to 10 wt %.

The preparations may contain additional inorganic UV filters, so-called particulate UV filters, in addition to the compounds of formulas I, II or III and the optional organic UV filters as described above.

These combinations with particulate UV filters are possible as both powders and also as dispersions or pastes of the following types.

Those from the group of titanium dioxides such as coated titanium dioxide (e.g., Eusolex® T-2000, Eusolex®T-AQUA, Eusolex®T-AVO, Eusolex®T-OLEO), zinc oxides (e.g., Sachtotec®), iron oxides or cerium oxides and/or zirconium oxides are preferred.

Furthermore, combinations with pigment titanium dioxide or zinc oxide are also possible, wherein the particle size of these pigments is greater than or equal to 200 nm, for example, Hombitan® FG or Hombitan® FF Pharma.

In addition, it may be preferably if the preparations contain inorganic UV filters aftertreated with the usual methods such as those described in Cosmetics & Toiletries, February 1990, Vol. 105, pp. 53-64. One or more of the following after-treatment components may be selected: amino acids, beeswax, fatty acids, fatty acid alcohols, anionic surfactants, lecithin, phospholipids, sodium, potassium, zinc, iron or aluminum salts of fatty acids, polyethylenes, silicones, proteins (especially collagen or elastin), alkanolamines, silicon dioxide, aluminum oxide, other metal oxides, phosphates such as sodium hexametaphosphate or glycerol.

Preferred particulate UV filters for use here include:
  Untreated titanium dioxides such as the products microtitanium dioxide MT 500 B from Tayca; titanium dioxide P25 from Degussa,
  After-treated micronized titanium dioxides with aluminum oxide and silicon dioxide aftertreatment, for example, the product "Microtitanium Dioxide MT 100 SA" from Tayca; or the product "Tioveil Fin" from Uniqema,
  After-treated micronized titanium dioxides with aluminum oxide and/or aluminum stearate/laurate after-treatment, for example, microtitanium dioxide MT 100 T from Tayca, Eusolex T-2000 from Merck,
  After-treated micronized titanium dioxides with iron oxide and/or iron stearate after-treatment, for example, the product microtitanium dioxide MT 100 F from Tayca,
  After-treated micronized titanium dioxides with silicon dioxides, aluminum oxide and silicone after-treatment, for example, the product "Microtitanium Dioxide MT 100 SAS" from Tayca,
  After-treated micronized titanium dioxides with sodium hexametaphosphates, for example, the product "Microtitanium Dioxide MT 150 W" from Tayca.

The treated micronized titanium dioxides used for the combination may also be after-treated with:
  Octyltrimethoxysilane, for example, the product Tego Sun T 805 from Degussa,
  Silicon dioxide, for example, the product Parsol T-X from DSM,
  Aluminum oxide and stearic acid, for example, the product UV-Titan M160 from Sachtleben,
  Aluminum and glycerol, for example, the product UV-Titan from Sachtleben,
  Aluminum and silicone oils, for example, the product UV-Titan M262 from Sachtleben,
  Sodium hexametaphosphate and polyvinylpyrrolidone,
  Polydimethylsiloxane, for example, the product "70250 Cardre UF TiO2Si3" from Cardre,
  Polydimethylhydrogen siloxanes, for example, the product "Microtitanium Dioxide USP Grade Hydrophobic" from Color Techniques.

Furthermore, a combination with the following products may also be advantageous:
  Untreated zinc oxides, for example, the product Z-Cote from BASF (Sunsmart), Nanox from Elementis,
  After-treated zinc oxides, for example, the following products:
    "Zinc oxide CS-5" from Toshibi (ZnO after-treated with polymethylhydrogen siloxane)
    Nanoguard zinc oxide FN from Nanophase Technologies
    "SPD-Z1" from Shin-Etsu (ZnO after-treated with a silicone-grafted acrylic polymer dispersed in cyclodimethylsiloxane)
    "Escalol Z100" from ISP (aluminum oxide after-treated ZnO dispersed in an ethylhexyl methoxycinnamate/PVP hexadecene/methicone copolymer blend)
    "Fuji ZNO-SMS-10" from Fuji Pigment (ZnO after-treated with silicon dioxide and polymethyl silsesquioxane);
    Untreated cerium oxide micropigment, for example, with the designation "colloidal cerium oxide" from Rhone Poulenc
    Untreated and/or after-treated iron oxide with the designation Nanogar from Arnaud.

For example, mixtures of different metal oxides, e.g., titanium dioxide and cerium oxide with and without after-treatment may also be used such as the product Sunveil A from Ikeda. Furthermore, mixtures of aluminum oxide, silicon dioxide and silicone after-treated titanium dioxide, zinc oxide mixtures, for example, the product UV-Titan M261 from Sachtleben may also be used.

These inorganic UV filters are usually incorporated into the preparations in an amount of 0.1 wt % to 25 wt %, preferably 2 wt % to 10 wt %.

By combining one or more of the aforementioned compounds with a UV filter effect, the protective effect against harmful influences of UV radiation can be optimized.

All the aforementioned UV filters may also be used in encapsulated form. In particular it is advantageous to use organic UV filters in encapsulated form.

The capsules are preferably contained in the preparations to be used according to the invention in amounts which ensure that the encapsulated UV filters are present in the preparation in the aforementioned wt % ratios.

In the preparations described here which contain at least one compound of formulas I, II or III according to the invention, pigments may also be present in them wherein the layer structure of the pigments is not limited.

The pigment should preferably be skin colored or brownish when used in the amount of 0.5 to 5 wt %. The choice of a corresponding pigment is a matter with which those skilled in the art are familiar.

Preferred preparations may also contain at least one additional cosmetic active ingredient, for example, selected from antioxidants, antiaging ingredients, anti-wrinkle ingredients, anti-dandruff ingredients, anti-acne ingredients, anti-cellulite ingredients, deodorants or vitamins.

The protective effect of preparations against oxidative stress and/or against the effects of radicals can be improved if the preparations contain one or more antioxidants, but it will not pose any problems for those skilled in the art to selected antioxidants having a rapid or time release effect.

There are many tried and tested substances known from the technical literature that can be used as antioxidants, for example, amino acids (e.g., glycine, histidine, tyrosine, tryptophan) and derivatives thereof, imidazoles, (e.g., urocanic acid) and derivatives thereof, peptides such as D,L-carnosine, D-carnosine, L-carnosine and derivatives thereof (e.g., anserine), carotinoids, carotenes (e.g., α-carotene, β-carotene, lycopene) and derivatives thereof, chlorogenic acid and derivatives thereof, lipoic acid and derivatives thereof (e.g., dihydrolipoic acid), aurothioglucose, propylthiouracil and other thiols (e.g., thioredoxin, glutathione, cysteine, cystine, cystamineand the glycosyl, n-acetyl, methyl, ethyl, propyl, amyl, butyl and lauryl, palmitoyl, oleyl, γ-linoleyl, cholesteryl and glyceryl esters thereof) as well as their salts, dilaurylthiodipropionate, distearylthiodipropionate, thiodipropionic acid and derivatives thereof (esters, ethers, peptides, lipids, nucleotides, nucleosides and salts) as well as sulfoximine compounds (e.g., buthionine sulfoximines, homocysteine sulfoximine, buthionine sulfone, penta-, hexa-, heptathionine sulfoximine) in very low tolerable doses (e.g., pmol to μmol/kg), also (metal) chelators (e.g., α-hydroxyfatty acids, palmitic acid, phytic acid, lactoferrin), α-hydroxy acids (e.g., citric acid, lactic acid, malic acid), humic acid, gallic acid, bile extracts, bilirubin, biliverdin, EDTA, EGTA, pentasodium ethylenediamine tetramethylene phosphonate and derivatives thereof, unsaturated fatty acids and derivatives thereof, vitamin C and derivatives (e.g., ascorbyl palmitate, magnesium ascorbyl phosphate, ascorbyl acetate), tocopherols and derivatives (e.g., vitamin Eacetate), vitamin Aand derivatives (e.g., vitamin A palmitate) as well as coniferylbenzoate of benzoic resin, rutic acid and derivatives thereof, α-glycosylrutin, ferulaic acid, furfurylidene glucitol, carnosine, butylhydroxytoluene, butylhydroxyanisole, nordohydroguaiaretic acid, trihydroxybutyrophenone, quercetin, uric acid and derivatives thereof, mannose and derivatives thereof, zinc and derivatives thereof (e.g., ZnO, ZnSO$_4$), selenium and derivatives thereof (e.g., selenium methionine), stilbenes and derivatives thereof (e.g., stilbene oxide, trans-stilbene oxide).

Suitable antioxidants also includes compounds of formulas A or B where
R$^1$ can be selected from the group —C(O)CH$_3$, —CO$_2$R$^3$, —C(O)NH2 and —C(O)N(R$^4$)$_2$,
X denotes O or NH,
R$^2$ denotes linear or branched alkyl with 1 to 30 carbon atoms,
R$^3$ denotes linear or branched alkyl with 1 to 20 carbon atoms,
R$^4$ independently of one another denotes H or linear or branched alkyl with 1 to 8 carbon atoms,
R$^5$ denotes H, linear or branched alkyl with 1 to 8 carbon atoms or linear or branched alkoxy with 1 to 8 carbon atoms and
R$^6$ linear or branched alkyl with 1 to 8 carbon atoms, preferably derivatives of 2-(4-hydroxy-3,5-dimethoxybenzylidene)malonic acid and/or 2-(4-hydroxy-3,5-dimethoxybenzyl)malonic acid, especially preferably 2-(4-hydroxy-3,5-dimethoxybenzylidene)malonic acid bis-(2-ethylhexyl) ester (e.g., Oxynex® ST Liquid) and/or 2-(4-hydroxy-3,5-dimethoxybenzyl)malonic acid bis-(2-ethylhexyl) ester (e.g., RonaCare® AP).

Mixtures of antioxidants are also suitable for use in the inventive cosmetic preparations. Known and commercially available mixtures include, for example, mixtures containing as the active ingredients lecithin, L-(+)-ascorbyl palmitate and citric acid, natural tocopherols, L-(+)-ascorbyl palmitate, L-(+)-ascorbic acid and citric acid (e.g., Oxynex® K LIQUID), tocopherolextracts from natural sources, L-(+)-ascorbyl palmitate, L-(+)-ascorbic acid and citric acid (e.g., Oxynex® L LIQUID), DL-α-tocopherol, L (+)-ascorbyl palmitate, citric acid and lecithin (e.g., Oxynex® LM) or butylhydroxytoluene (BHT), L-(+)-ascorbyl palmitate and citric acid (e.g., Oxynex® 2004). Such antioxidants are generally used with the compounds according to the invention in such compositions in wt % ratios in the range of 1000:1 to 1:1000, preferably in weight percentage ratios of 100:1 to 1:100.

Of the phenols that can be used according to the invention, the polyphenols some of which occur as natural substances, are of particular interest for applications in pharmaceutical, cosmetic or nutritional fields. For example, the flavonoids or bioflavonoids which are known mainly as plant dyes often have an antioxidant potential. Effects of the substitution pattern of mono- and dihydroxyflavones have been studied by K. Lemanska, H. Szymusiak, B. Tyrakowska, R. Zielinski, I. M. C. M. Rietjens; Current Topics in Biophysics, 2000, 24(2), 101-108. It is observed there that dihydroxyflavones with an OH group in proximity to the keto function or OH groups in 3'4'- or 6,7- or 7,8-position do have antioxidant properties while other mono- and dihydroxyflavones have no antioxidant properties in some cases.

Quercetin (cyanidanole, cyanidenolone 1522, meletin, sophoretin, ericin, 3,3',4',5,7-pentahydroxyflavone) is often mentioned as a particularly effective antioxidant (e.g., C. A. Rice-Evans, N. J. Miller, G. Paganga, Trends in Plant Science 1997, 2(4), 152-159). K. Lemanska, H. Szymusiak, B. Tyrakowska, R. Zielinski, A. E. M. F. Soffers and I. M. C. M. Rietjens (Free Radical Biology & Medicine 2001, 31(7), 869-881) investigate the pH dependence of the antioxidant effect of hydroxyflavones. Quercetin has the highest activity of all the structures investigated over the entire pH range.

Suitable antiaging active ingredients in particular for skin care preparations are preferably so-called compatible solutes. These are substances that are involved in the osmoregulation of plants or microorganisms and can be isolated from these organisms. The osmolytes described in the German Patent Application DE-A-10133202 are also included under the heading of compatible solutes. Suitable osmolytes include, for example, polyols, methylamine compounds and amino acids as well as their precursors. Osmolytes in the sense of German Patent Application DE-A-10133202 are understood in particular to include substances from the group of polyols such as, for example, myoinositol, mannitol or sorbitol and/or one or more of the following osmolytically active substances: taurine, choline, betaine, phosphorylcholine, glycerophosphorylcholine, glutamine, glycine, α-alanine, glutamate, aspartate, proline and taurine. Precursors of these substances include, for example, glucose, glucose polymers, phosphatidylcholine, phosphatidylinositol, inorganic phosphates, proteins, peptides and polyamino acids. Precursors are, for example, compounds that are converted into osmolytes by metabolic steps.

The compatible solutes used according to the invention are preferably substances selected from the group consisting of pyrimidine carboxylic acids (such as ectoin and hydroxyectoin, proline, betaine, glutamine, cyclic diphosphoglycerate, N-acetylornithine, trimethylamine N-oxide, dimyoinositol phosphate (DIP), cyclic 2,3-diphosphoglycerate (cDPG), 1,1-diglycerol phosphate (DGP), ß-mannosyl glycerate (firoin), ß-mannosyl glyceramide (firoin-A) or/and dimannosyldiinositolphosphate (DMIP) or an optical isomer, derivative, e.g., an acid, a salt or ester of these compounds or combinations thereof.

Of the pyrimidine carboxylic acids, particularly suitable examples include ectoin ((S)-1,4,5,6-tetrahydro-2-methyl-4-pyrimidine carboxylic acid) and hydroxyectoin ((S,S)-1,4,5,6-tetrahydro-5-hydroxy-2-methyl-4-pyrimidine carboxylic acid) and derivatives thereof.

Additional antiaging active ingredients that may be used include products from Merck such as 5,7-dihydroxy-2-methylchromon, marked under the brand name RonaCare®Luremine, Ronacare®Isoquercetin, Ronacare®Tilirosid or Ronacare®Cyclopeptide 5.

The preparations to be used may also contain vitamins as additional ingredients. Preferred vitamins and vitamin derivatives include those selected from vitamin A, vitamin A propionate, vitamin Apalmitate, vitamin Aacetate, retinol, vitamin B, thiamine chloride hydrochloride (vitamin $B_1$), riboflavin (vitamin B2), nicotinamide, vitamin C (ascorbic acid), vitamin D, ergocalciferol (vitamin $D_2$), vitamin E, DL-α-tocopherol, tocopherolEacetate, tocopherolhydrogensuccinate, vitamin $K_1$, esculin (vitamin P active ingredient), thiamine (vitamin $B_1$), nicotinic acid (niacin), pyridoxine, pyridoxal, pyridoxamine (vitamin $B_6$), pantothenic acid, biotin, folic acid and cobalamine (vitamin B12), in particular preferably vitamin Apalmitate, vitamin C and derivatives thereof, DL-α-tocopherol, tocopherol Eacetate, nicotinic acid, pantothenic acid and biotin. The vitamins are usually added with the premixes or preparations containing flavonoids, usually in amounts in the range of 0.01 to 5.0 wt %, based on the total weight, when used in cosmetic preparations. Applications in nutritional physiology are usually based on the respective recommended vitamin needs.

The retinoids that have been described are at the same time also effective anti-cellulite ingredients. Caffeine is another well known anti-cellulite active ingredient.

The subject matter of the present invention is also a method for producing a preparation as described above which is characterized in that at least one compound of formulas I, II or III is mixed with a vehicle suitable for topical preparations and optionally with auxiliary substances and/or fillers. Suitable vehicle substances as well as auxiliary or filler substances are described in detail in the following section.

The aforementioned ingredients of the preparation can be incorporated in the usual ways with the help of techniques with which those skilled in the art are familiar The cosmetic and dermatologic preparations may be present in various forms. For example, they may be in the form of a solution, an anhydrous preparation, an emulsion or microemulsion of the water-in-oil (W/O) type or of the oil-in-water (O/W) type, a multiple emulsion, for example, of the water-in-oil-in-water (W/O/W) type or the O/W/O type, a gel, a solid stick, an ointment or an aerosol. Emulsions are preferred and O/W emulsions are especially preferred. Emulsions, W/O emulsions and O/W emulsions can be obtained by the usual methods.

The following can be listed as application forms of the preparations to be used, for example: solutions, suspensions, emulsions, PIT emulsions, pastes, ointments, gels, creams, lotions, powders, soaps, surfactant-containing cleaning preparations, oils, aerosols, patches, wrappings, dressings and sprays.

Preferred auxiliary substances originate from the group of preservatives, stabilizers, solubilizers, coloring agents and odor improvers.

Ointments, pastes, creams and gels may contain the usual vehicle substances suitable for topical administration, for example, animal and vegetable fats, waxes, paraffins, starch, gum tragacanth, cellulose derivatives, polyethylene glycols, silicones, bentonites, silicic acid, talc and zinc oxide or mixtures of these substances.

Powders and sprays may contain the usual vehicle substances, for example, lactose, talc, silicic acid, aluminum hydroxide, calcium silicate and polyamide powders or mixtures of these substances. Sprays may additionally contain the usual volatile liquefied propellants, for example, chlorofluorocarbons, propane/butane or dimethyl ether. Compressed air may also be used to advantage.

Solutions and emulsions may contain the usual vehicle substances such as solvents, solubilizers and emulsifiers, for example, water, ethanol, isopropanol, ethyl carbonate, ethyl acetate, benzyl alcohol, benzyl benzoate, propylene glycol, 1,3-butyl glycol, oils, in particular cottonseed oil, peanut oil, corn oil, olive oil, castor oil and sesame oil, XTend 226 (L'Oréal), glycerin fatty acid esters, polyethylene glycols and fatty acid esters of sorbitan or mixtures of these substances.

A preferred solubilizer in general is 2-isopropyl-5-methylcyclohexanecarbonylD-alaninemethyl ester Suspensions may contain the usual vehicle substances such as liquid diluents, for example, water, ethanol or propylene glycol, suspension agents, for example, ethoxylated isostearyl alcohols, polyoxyethylene sorbitol ester and polyoxyethylene sorbitan ester, microcrystalline cellulose, aluminum metahydroxide, bentonite, agar and gum tragacanth or mixtures of these substances.

Soaps may contain the usual vehicle substances such as alkali salts or fatty acids, salts of fatty acid hemiesters, fatty acid protein hydrolyzates, isothionates, lanolin, fatty alcohol, vegetable oils, plant extracts, glycerin, sugar or mixtures of these substances.

Cleaning products that contain surfactants may also contain the usual vehicle substances such as the salts of fatty alcohol sulfates, fatty alcohol ether sulfates, sulfosuccinic acid hemiesters, fatty acid protein hydrolyzates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerin fatty acid esters or mixtures of these substances.

Face and body oils may contain the usual vehicle substances such as synthetic oils such as fatty acid esters, fatty alcohols, silicone oils, natural oils such as vegetable oils and oil-based plant extracts, paraffin oils, lanolin oils or mixtures of these substances.

Other typical cosmetic application forms also include lipstick, lip care sticks, powder, emulsion and wax makeup as well as sunscreen, pre-sun and after-sun preparations.

The preferred preparation forms also include in particular emulsions.

Emulsions are advantageous and contain, for example, the aforementioned fats, oils, waxes and other fatty substances as well as water and an emulsifier such as those generally used for such a type of preparation.

The lipid phase can advantageously be selected from the following substance group:
  Mineral oils, mineral waxes;
  Oils such as triglycerides of capric acid or caprylic acid as well as natural oils such as castor oil;
  Fats, waxes and other natural and synthetic fatty substances, preferably esters of fatty acids with alcohols of a low carbon number, for example, with isopropanol, propylene glycol or glycerin or esters of fatty alcohols with alkanoic acids with a low number of carbon atoms or with fatty acids;
  Silicone oils such as dimethylpolysiloxanes, diethylpolysiloxanes, diphenylpolysiloxanes and mixed forms thereof.

The oil phase of the emulsions, oleogels and/or hydrodispersions or lipodispersions in the sense of the present invention is advantageously selected from the group of esters of saturated or unsaturated, branched and/or unbranched alkane carboxylic acids with a chain length of 3 to 30 carbon atoms and saturated and/or unsaturated, branches and/or unbranched alcohols with a chain length of 3 to 30 carbon atoms, from the group of esters of aromatic carboxylic acid and saturated and/or unsaturated, branched and/or unbranched alcohols with a chain length of 3 to 30 carbon atoms. Such ester oils may then advantageously be selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexaldecyl stearate, 2-octyldodecyl palmitate, oleyl oleate, oleyl erucate, erucyl oleate, erucyl erucate as well as synthetic, semisynthetic and natural mixtures of such esters, for example, jojoba oil.

Furthermore, the oil phase may advantageously be selected from the group of branched and unbranched hydrocarbons and hydrocarbon waxes, silicone oils, dialkyl ethers, the group of saturated or unsaturated, branched or unbranched alcohols as well as the fatty acid triglycerides namely the triglycerol esters of saturated and/or unsaturated, branched and/or unbranched alkane carboxylic acids with a chain length of 8 to 24, in particular 12 to 18 carbon atoms. The fatty acid triglycerides may advantageously be selected from the group of synthetic, semisynthetic and natural oils, for example, olive oil, sunflower oil, soy oil, peanut oil, canola oil, almond oil, palm oil, coconut oil, palm kernel oil and the like.

Any blends of such oil and wax components can also be used advantageously in the sense of the present invention. It may optionally also be advantageous to use waxes, for example, cetyl palmitate as the sole lipid component of the oil phase.

The aqueous phase of the preparations to be used optionally also contains alcohols, diols or polyols with a low carbon number as well as their ethers, preferably ethanol, isopropanol, propylene glycol, glycerin, ethylene glycol, ethylene glycol monoethyl or monobutyl ether, propylene glycol monomethyl ether, monoethyl ether or monobutyl ether, diethylene glycol monomethyl ormonoethyl ether and similar products, as well as the alcohols with a low carbon number, for example, ethanol, isopropanol, 1,2-propanediol, glycerin and in particular one or more thickeners, which may advantageously be selected from the group of silicon dioxide, aluminum silicates, polysaccharides and/or derivatives thereof, for example, hyaluronic acid, xanthan gum, hydroxypropylmethyl cellulose, especially advantageously from the group of polyacrylates, preferably a polyacrylate from the group of so-called carbopols, for example, carbopols of types 980, 981, 1382, 2984, 5984, each individually or in combination.

Mixtures of the aforementioned solvents are used in particular. Water may be an additional ingredient when using alcoholic solvents.

In a preferred embodiment, the preparations to be used contain hydrophilic surfactants. The hydrophilic surfactants are preferably selected from the group of alkyl glucosides, acyl lactylates, betaines and cocoamphoacetates.

The emulsifiers used may be the known W/O and O/W emulsifiers, for example. It is advantageous to use additional conventional co-emulsifiers in the preferred O/W emulsions.

For example, O/W emulsifiers mainly from the group of substances with HLB values of 11-16, most especially advantageously with HLB values of 14.5-15.5, if the O/W emulsifiers have saturated R and R' radicals, are advantageously used as the co-emulsifiers. If the co-emulsifiers contain unsaturated R and/or R' radicals or if there are isoalkyl derivatives, then the preferred HLB value of such emulsifiers may also be lower or higher.

It is advantageous to select fatty alcohol ethoxylate from the group of ethoxylated stearyl alcohols, cetyl alcohols, cetyl stearyl alcohols (cetearyl alcohols).

It is also advantageous to select the fatty acid ethoxylates from the following group:
  polyethylene glycol 20-stearate, polyethylene glycol 21-stearate, polyethylene glycol 22-stearate, polyethylene glycol 23-stearate, polyethylene glycol 24-stearate, polyethylene glycol 25-stearate, polyethylene glycol 12-isostearate, polyethylene glycol 13-isostearate, polyethylene glycol 14-isostearate, polyethylene glycol 15-isostearate, polyethylene glycol 16-isostearate, polyethylene glycol 17-isostearate, polyethylene glycol 18-isostearate, polyethylene glycol 19-isostearate, polyethylene glycol 20-isostearate, polyethylene glycol 21-isostearate, polyethylene glycol 22-isostearate, polyethylene glycol 23-isostearate, polyethylene glycol 24-isostearate, polyethylene glycol 25-isostearate, polyethylene glycol 12-oleate, polyethylene glycol 13-oleate, polyethylene glycol 14-oleate, polyethylene glycol 15-oleate, polyethylene glycol 16-oleate, polyethylene glycol 17-oleate, polyethylene glycol 18-oleate, polyethylene glycol 19-oleate, polyethylene glycol 20-oleate.

Sodium laureth 11-carboxylate can be used to advantage as the ethoxylated alkyl ether carboxylic acid and/or salt thereof. Sodium laureth 14-sulfate can be used to advantage as the alkyl ether sulfate. Polyethylene glycol-30 cholesteryl ether can be used to advantage as the ethoxylated cholesterol derivative. Polyethylene glycol 25-soy sterol has proven successful. Polyethylene glycol-60 evening primrose glycerides can also be used to advantage as the ethoxylated triglycerides.

In addition, it is advantageous to select the polyethylene glycol glycerin fatty acid esters from the group of polyethylene glycol 20-glyceryl laurate, polyethylene glycol 21-glyceryl laurate, polyethylene glycol 22-glyceryl laurate, polyethylene glycol 23-glyceryl laurate, polyethylene glycol 6-glyceryl caprate/caprinate, polyethylene glycol 20-glyceryl oleate, polyethylene glycol 20-glyceryl isostearate, polyethylene glycol 18-glyceryl oleate (cocoate).

It is also advantageous to select the sorbitan esters from the group of polyethylene glycol 20-sorbitan monolaurate, polyethylene glycol 20-sorbitan monostearate, polyethylene glycol 20-sorbitan monoisostearate, polyethylene glycol 20-sorbitan monopalmitate, polyethylene glycol 20-sorbitan monooleate.

Optional W/O emulsions that are nevertheless advantageous according to the invention for use here include: fatty alcohols with 8 to 30 carbon atoms, monoglycerin esters of saturated and/or unsaturated branched and/or unbranched alkane carboxylic acids with a chain length of 8 to 24 carbon atoms, in particular 8 to 18 carbon atoms, diglycerin esters of saturated and/or unsaturated branched and/or unbranched alkane carboxylic acids with a chain length of 8 to 24 in particular 12 to 18 carbon atoms, monoglycerin ethers of saturated and/or unsaturated, branched and/or unbranched alcohols with a chain length of 8 to 24, in particular 12 to 18 carbon atoms, diglycerin ethers of saturated and/or unsaturated, branched and/or unbranched alcohols with a chain length of 8 to 24, in particular 12 to 18 carbon atoms, propylene glycol esters of saturated and/or unsaturated, branched and/or unbranched alkane carboxylic acids with a chain length of 8 to 24 in particular 12 to 18 carbon atoms as well as sorbitan esters of saturated and/or unsaturated, branched and/or unbranched alkane carboxylic acids with a chain length of 8 to 24 in particular 12 to 18 carbon atoms.

W/O emulsifiers that are advantageous in particular include glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol 2-stearyl ether (steareth-2), glyceryl monolaurate, glyceryl monocaprinate, glyceryl monocaprylate or PEG-30-dipolyhydroxystearate.

The preparation may contain cosmetic adjuvants which are generally used in this type of preparation such as thickeners, softeners, humectants, surfactants, emulsifiers, preservatives, antifoaming agents, perfumes, waxes, lanolin, propellants, coloring agents and/or pigments and other ingredients normally used in cosmetics.

An oil, a wax or some other fatty substance, a low monoalcohol or a low polyol or mixtures thereof may be used as the dispersant and/or solubilizing agent. Especially preferred monoalcohols or polyols include ethanol, isopropanol, propylene glycol, glycerol and sorbitol.

A preferred embodiment of the invention is an emulsion which is in the form of a protection cream or milk and contains, for example, fatty alcohols, fatty acids, fatty acid esters, in particular triglycerides of fatty acids, lanolin, natural and synthetic oils or waxes and emulsifiers in the presence of water.

Additional preferred embodiments include oil-based lotions containing natural or synthetic oils and waxes, lanolin, fatty acid esters, in particular triglycerides of fatty acids or oligoalcoholic lotions based on a low alcohol such as ethanol or a glycerol such as propylene glycol and/or a polyol such as glycerin and oils waxes and fatty acid esters such as triglycerides of fatty acids.

The preparation may also be present in the form of an alcoholic gel comprising one or more low alcohols or polyols such as ethanol, propylene glycol or glycerol and a thickener such as diatomaceous earth. The oily-alcoholic gels also contain natural or synthetic oil or wax.

The solid sticks are made of natural or synthetic waxes and oils, fatty alcohols, fatty acids, fatty acid esters, lanolin and other fatty substances.

If a preparation is formulated as an aerosol, it is customary to use the conventional propellants such as alkanes, fluoroalkanes and chlorofluoroalkanes, preferably alkanes.

Another subject matter of the present invention is compounds of formulas I, II or III where R stands for a radical selected from the group consisting of rhamnosyl, arabinosyl, galacturonide, glucuronide, 2-(acetylamino)-2-deoxyglucosyl, mannosyl, allosyl, fucosyl and xylosyl, wherein each of the radicals may be present in the form of the D- or L-enantiomer and as an α- or β-anomer, wherein compounds of formula I wherein R is an allosyl are excluded.

The compounds are preferably selected from the compounds of formula I or II.

R in the compounds of formula I, II or III especially preferably stands for rhamnosyl.

In a most especially preferred embodiment, the compound of formula I or II is selected from the compounds 7-O-α-L-rhamnosylnoreugenin (Ib) or 5-O-α-L-rhamnosyl-noreugenin (IIa).

Even without additional embodiments, it is assumed that those skilled in the art will be able to make use of the above description in the broadest extent. The preferred embodiments and examples are therefore to be interpreted only as descriptive disclosure but by no means as disclosure that is limiting in any way. The complete disclosure of all the patent applications and publications listed above and below is introduced into the present patent application by reference thereto.

Other important features and advantages of the invention are derived from the dependent claims and the examples.

The examples should illustrate the present invention without limiting its scope in any way.

EXAMPLES

Example 1: Experimental Procedure: Evaluating the Tanning Properties of the Test Preparations Using Reconstituted Human Epidermis with Melanocytes of Phototype II The epidermis with melanocytes of phototype II is reconstituted in an air/liquid interface system (directly at the air-liquid interface) in a culture medium from day 0 to day 4 for a complete differentiation. The culture is then continued from day 4 to day 14 in this same medium but without bovine pituitary extract (BPE). The test preparations were administered in the cooling medium from day 4 to day 14. The medium and the test preparations are each added on day 4, day 7 and day 11. DMSO and THF are tested in parallel and IBMX (100 µM) is used as the positive reference.

Example 2: Experimental Procedure: Semiquantification of the Melanin Content by Fontana-Masson Staining and Image Analysis After embedding in paraffin, a Fontana-Masson staining of the tissue sections is performed. The microscope slides are covered with a special medium and examined using a light microscope of the Leica DM2000 type with a digital camera. After staining, images are recorded and a quantification is performed by image analysis (on the basis of 12 images). For quantification of the melanin content in each image, the Leica QWin3 software is used. Two measurements are carried out. The first measurement gives the total intensity of the coloration, i.e., a lighter or darker melanin is reflected. The second measurement relates to the marked image area, i.e., the area of the epidermis containing the melanin. In these measurements all cell layers except the stratum corneum are included.

Example 3: Tanning Properties of the Substances (Ia), (Ib) and (IIa)

The procedure used was the same as that carried out in example 1 and 2. After determining the cytotoxic concentrations, substance (Ia) is tested at 8 µM, substance (Ib) at 40 µM (solvent: 0.1% THF) and substance (IIa) at 20 µM (solvent: 0.1% DMSO).

| Preparation | Quantification after Fontana-Masson staining |
|---|---|
| Quantification relative to the untreated controls | |
| IBMX (100 µM) | 152% ($p < 0.05$) |
| Substance (Ia, 8 µM) | 125% |
| Substance (Ib, 40 µM) | 174% ($p < 0.05$) |
| Substance (IIa, 20 µM) | 143% ($p < 0.05$) |

For IBMX a significant increase in the melanin content relative to the untreated controls is found. The same thing is true for substance (Ib) relative to THF and substance (IIa) relative to DMSO. For substance (Ia) an unambiguous tendency to increase pigmentation was detected.

Tanning properties of the substances (Ib) and (IIa), of a mixture of the two substances and rhamnose by itself In a second experiment the substances (Ib) and (IIa), a mixture of the two substances and rhamnose alone for comparison of the sugar radical.

The procedure was the same as that described in Examples 1 and 2.

After determining the cytotoxic concentrations of these substances, substance (Ib) is tested at 40 µM in DMSO (0.1%), substance (IIa) is tested at 20 µM in DMSO (0.1%), the mixture of (Ib)/(IIa) is tested at 40/20 µM in DMSO (0.1% and rhamnose is tested at 40 µM in THF (0.2%).

The results obtained have confirmed the findings of the first study.

| Preparation | Quantification after Fontana-Masson staining |
|---|---|
| Quantification relative to the untreated controls | |
| IBMX (100 µM) | 150% ($p < 0.01$) |
| Rhamnose (40 µM) | 109% |
| Substance (Ib, 40 µM) | 167% ($p < 0.01$) |
| Substance (IIa, 20 µM) | 147% ($p < 0.05$) |
| Mixture (Ib/IIa, 40 µM/20 µM) | 140% |

For IBMX a significant increase in the melanin content relative to the untreated controls was found. The same thing is also true of substance (Ib) relative to DMSO and substance (IIa) relative to DMSO. For the mixture (Ib/IIa) a definite tendency to increase pigmentation was detected. With rhamnose the tendency to increase melanin synthesis is only faintly pronounced.

Example 5: Production of Noreugenin 5-Rhamnoside (IIa) and Noreugenin 7-Rhamnoside (Ib)

The biotransformation is carried in a fermentative process in 3 liter agitated Erlenmeyer flasks with a fermentation volume of 500 mL. To this were added the transgenic strains E. coli BL21 (DE3) pET19::mgtB for the glucosylation or E. coli Rosetta gami 2 (DE3) pET19::gtfC were tested in Luria-Bertani (LB) complex medium at 28° C. and found to have an optical density ($OD_{600}$) of 0.8. By adding 50 µM isopropyl-β-D-thiogalactopyranoside (IPTG), the glycosyl transferase is expressed overnight at 17° C. Then the cells are centrifuged for 20 minutes at 17° C. and 7500 g and then resuspended in 0.1M phosphate buffer with 0.15M sodium chloride. To this culture are added 1 (w/v) % glucose and 0.2 mM noreugenin for the reaction and incubated further at 28° C. After 24 hours, the reaction is terminated by centrifuging the cells at 4° C. and 10,000 g for 20 minutes. The glycosides are in the supernatant after the reaction and are isolated by means of chromatographic purification. The first separation step takes place on an RT 250-10 Pharm prep column 100 RP-18e (10 µm) from Merck. The entire culture supernatant is enriched on the column by means of the pump system at a flow rate of 10 mL/min on the preparative HPLC system 1260 Infinity from Agilent and then eluted from the column again with a linear gradient of ascending acetonitrile concentration and thereby fractionated.

The preparative RP18-HPLC method as well as the analytical RP18 methods are based on a step gradient with the eluents A ($H_2O$+0.01% (v:v) trifluoroacetic acid) and eluent B (acetonitrile+0.01% (v:v) trifluoroacetic acid) having the following steps:
0-10 min 5% B,
10-20 min 10% B,
20-30 min 15% B,
30-40 min 20% B,
40-50 min 30% B,
50-60 min 100% B,
60-70 min 5% B.

Figure 1:
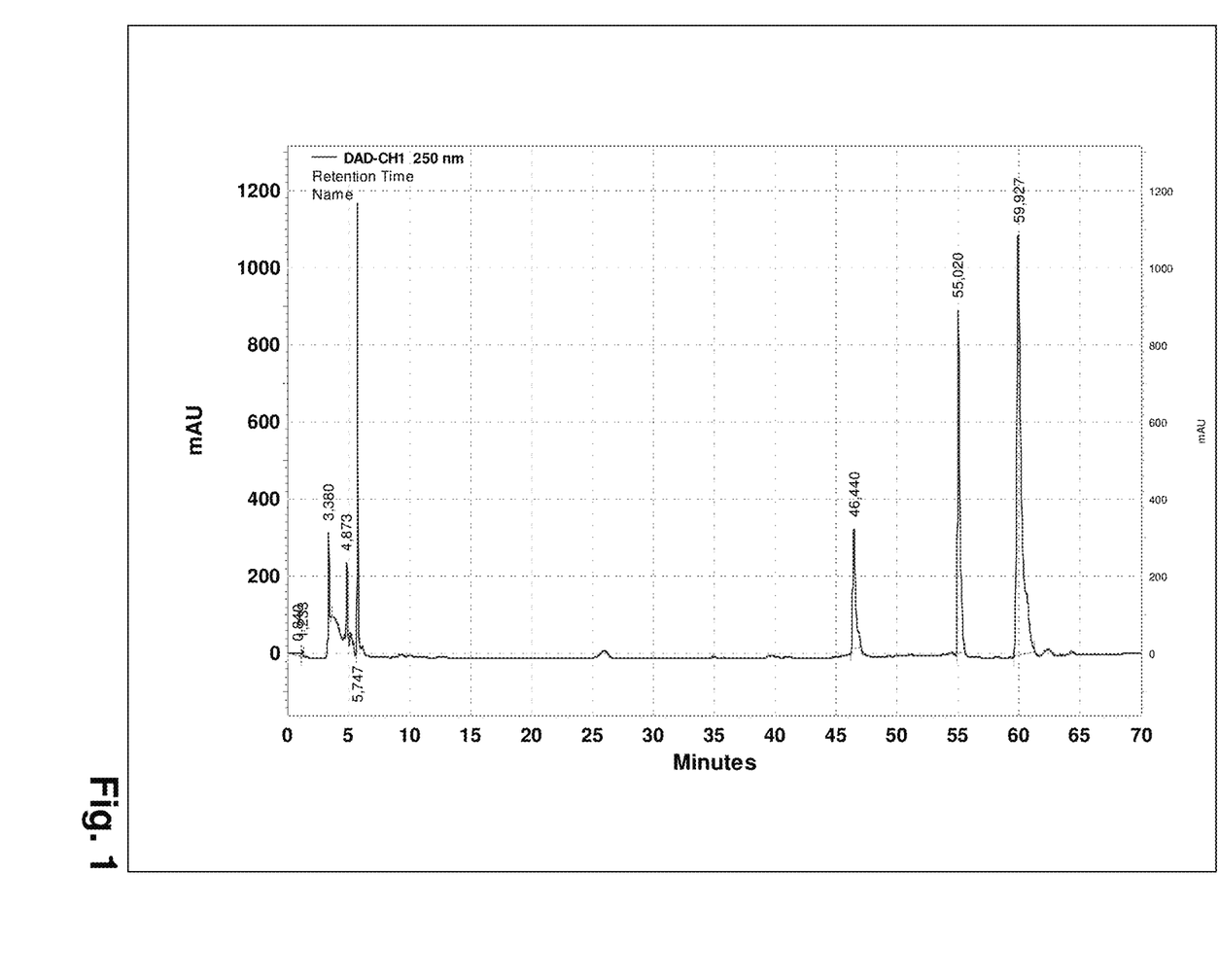
FIG. 1: Biotransformation after 6 hours to produce noreugenin rhamnosides. The annotated peaks from left to right are noreugenin 5-rhamnoside, noreugenin 7-rhamnoside, noreugenin with corresponding retention times of 46 min, 55 min and 60 min.

Even in the first chromatography step, the individual compounds can be separated well from one another (see FIG. 1). Acetonitrile is removed using an evaporator from Büchi Labortechnik GmbH and the aqueous solution of the individual noreugenin glycosides is lyophilized. The dried powder is dissolved in 30% acetonitrile (v:v). The second purification step for separation of the remaining impurities is carried out using a Hypersil Gold PFP (pentafluorophenyl) phase 250×4.6 mm from Thermo Scientific on a VWR Hitachi LaChrom Elite system. An isocratic run with 30% acetonitrile and a flow of 1 mL/min yields the target substances in a purity of more than 95%. The pure substances are dried, thus yielding a lyophilized powder.

For the analysis and process control, analytical HPLC with a diode array detector (VWR Hitachi see above) and mass spectrometry are performed. Mass spectrometric data is recorded using the microOTOF-Q with electron spray ionization (ESI) from Bruker Dalton. The samples are measured in the negative ion mode and injected using a syringe pump at a flow rate of 200 µL/min.

FIG. 1 shows the supernatant of a fermentation process after a reaction time of 6 hours. The non-glycosylated starting material noreugenin elutes at a retention time of 60 minutes. The noreugenin 7-rhamnoside has a retention time of 55 minutes, and the most hydrophilic molecule is noreugenin 5-rhamnoside with a retention time of 46 minutes.

Figure 2:
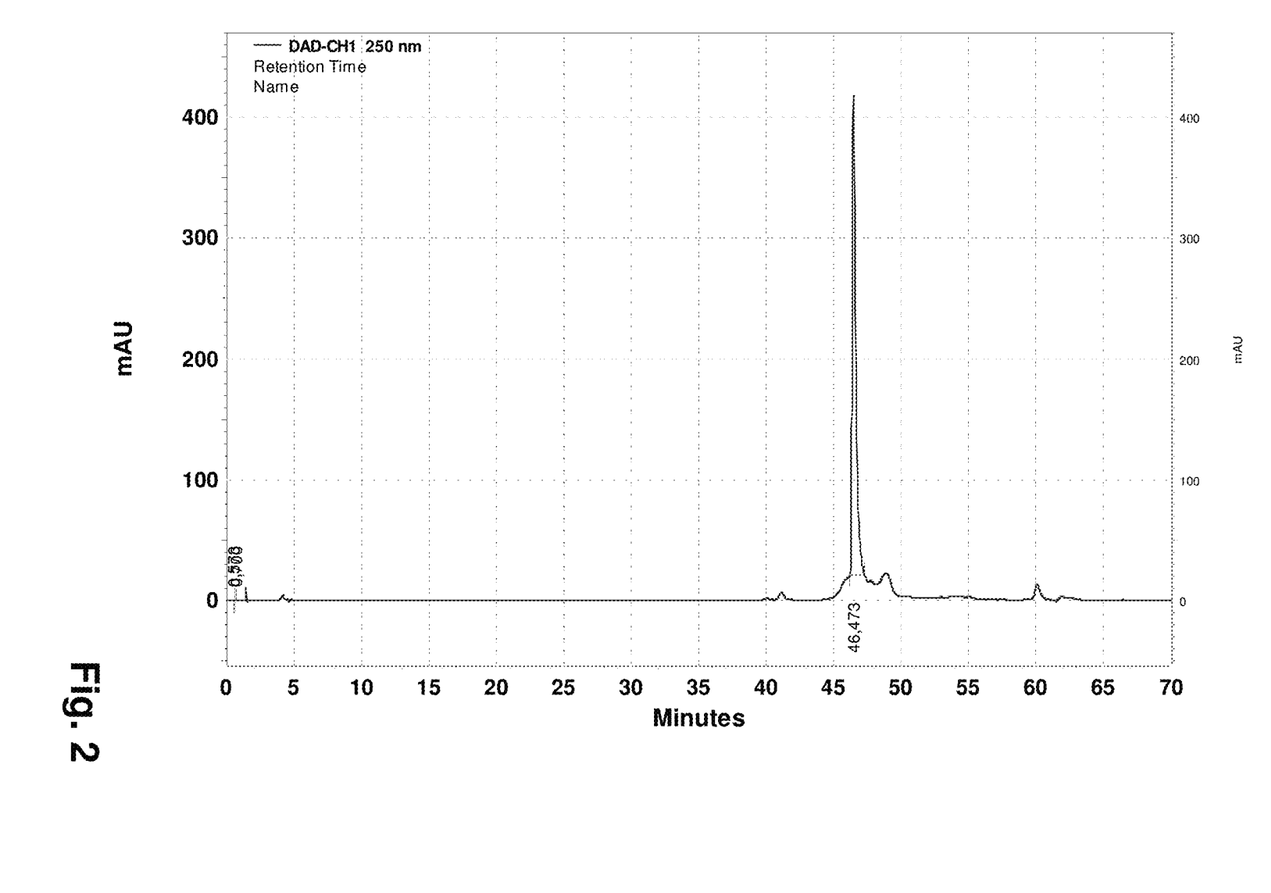
FIG. 2: RP18 chromatogram of noreugenin 5-rhamnoside.
Figure 3:
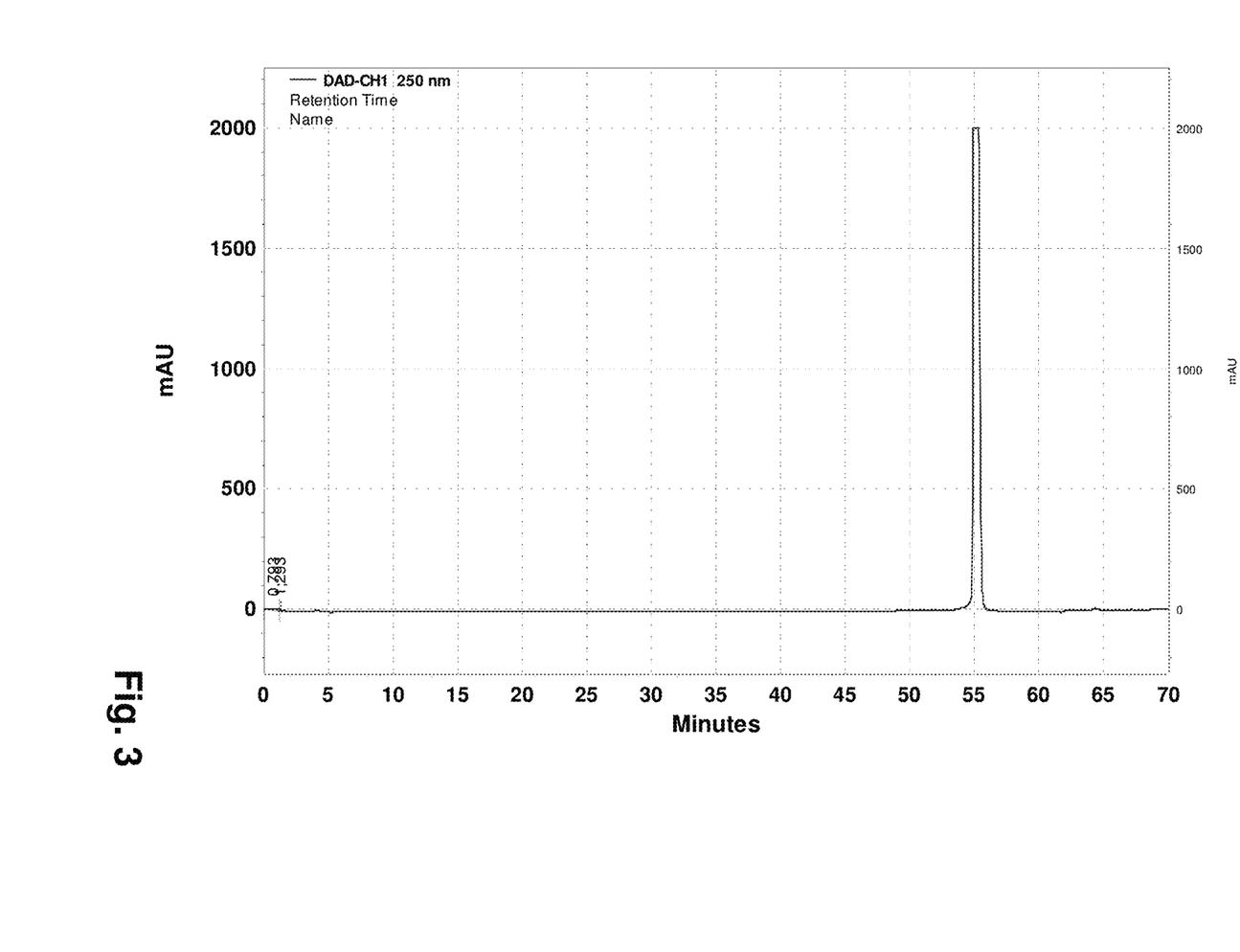
FIG. 3: RP18 chromatogram of noreugenin 7-rhamnoside.

The purified products are illustrated in FIGS. 2 and 3 and show a purity of >95% deteiniined by HPLC.

Figure 4:
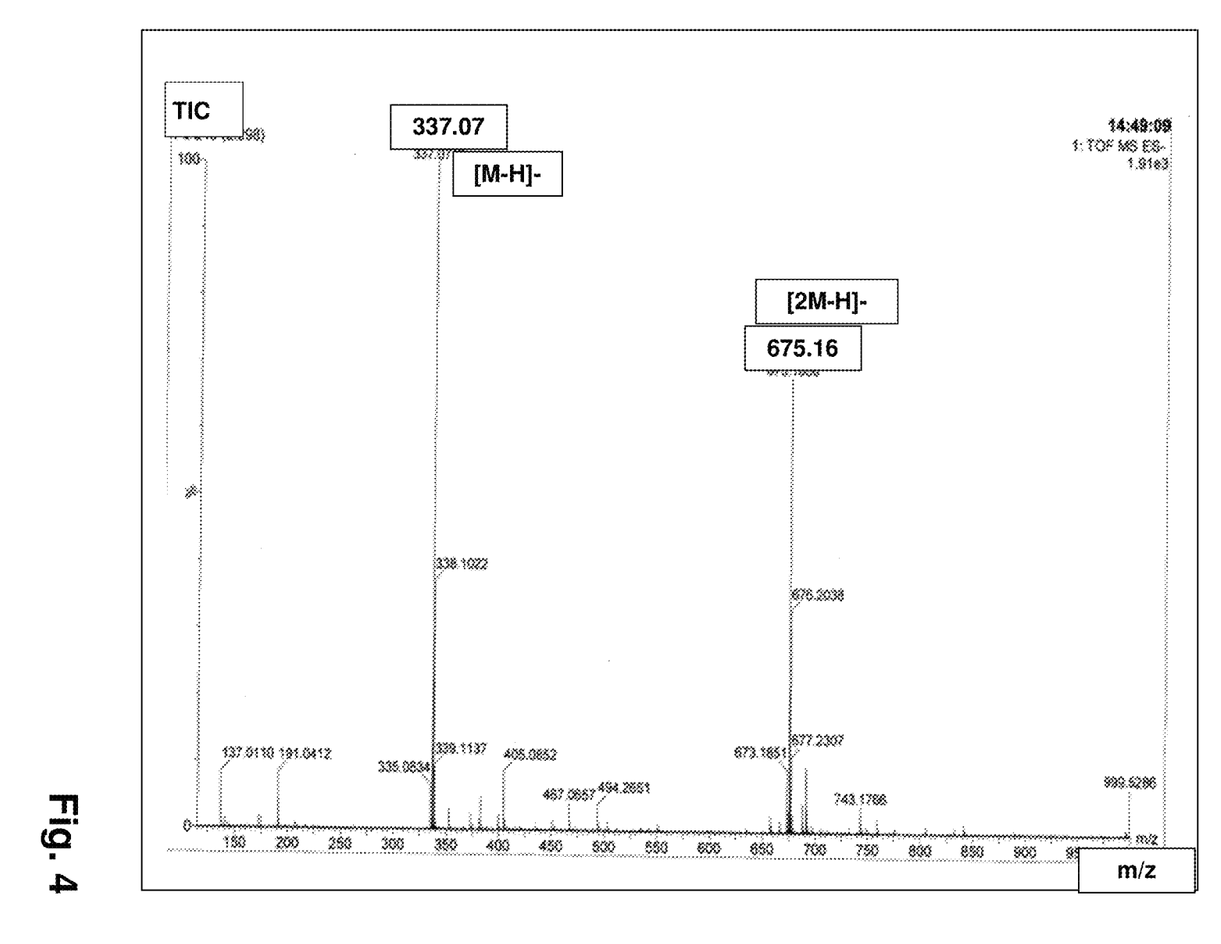
FIG. 4: Ion scan of noreugenin rhamnosides.

For unambiguous identification, the mass of the aforementioned fractions is determined. In the negative ion mode, the rhamnosides are presented as shown in FIG. 4. The molecule has a single charge and a molecular weight of m/z 337. Two molecules stored together and showing a charge appear as a mass of m/z 675 in the mass spectrum.

NMR data on noreugenin 5-rhamnoside (IL):
$^1$H-NMR (DMSO-☐, 400 MHz): δ=6.62 (d, 1H, J=2.2 Hz), 6.58 (d, 1H, J=2.2 Hz), 5.99 (d, 1H), 5.38 (d, 1H), 4.00 (s, 1H), 3.89-3.92 (dd, 1H, $J_1$=3.10 Hz, $J_2$=9.2 Hz), 3.49-3.54 (m, 7H), 3.36 (m, 1H), 2.30 (s, 3H).

The invention claimed is:

1. A method for tanning, comprising applying to skin a self-tanning substance comprising at least one compound of the formula I or II wherein R stands for rhamnosyl, and wherein the radical R may be in the form of a D- or L-enantiomer or an α- or β-anomer.

2. The method according to claim 1, wherein said self-tanning substance is applied to skin until to increase melanin synthesis, improve melanin transport and/or improve the distribution of melanin in suprabasal strata.

3. The method according to claim 1, wherein the compound of formula I is 7-O-α-L-rhamnosylnoreugenin (7-[(6-deoxy-α-L-mannopyranosyl)oxy]-5-hydroxy-2-methyl-4H-1-benzopyran-4-one) (Ib) and the compound of formula II is 5-O-α-L-rhamnosylnoreugenin (5-[(6-deoxy-α-L-mannopyranosyl)oxy]7-hydroxy-2-methyl-4H-1-benzopyran-4-one)(IIa).

4. A method for producing a preparation according to claim 3, wherein the at least one compound of formulas I or II is mixed with a vehicle suitable for topical application.

5. A preparation containing at least one compound of formulas I or II wherein R stands for the radical rhamnosyl, and wherein R may be present as a D- or L-enantiomer or an α- or β-anomer,
as well as a cosmetically suitable vehicle.

6. The preparation according to claim 5, wherein the at least one compound of formulas I or II is present in an amount of 0.01 to 10 wt %.

7. The preparation according to claim 5, wherein the preparation contains at least one additional self-tanning substance.

8. A compound of formulas I or II

I

-continued

II wherein R stands for rhamnosyl, wherein R may be present in the form of a D- or L-enantiomer or an α- or β-anomer.

9. The compound according to claim 8, wherein the compound of formula I is 7-O-α-L-rhamnosylnoreugenin (Ib) and the compound of formula II is 5-O-α-L-rhamnosylnoreugenin (IIa).

* * * * *